United States Patent
DeVerter et al.

(10) Patent No.: US 8,140,354 B2
(45) Date of Patent: *Mar. 20, 2012

(54) ORDERING CLINICAL ORDERS ASSOCIATED WITH FUTURE EVENTS

(75) Inventors: John Q. DeVerter, Liberty, MO (US); Michael A. Ash, Parkville, MO (US); Yegor F. Hanov, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/264,725

(22) Filed: Nov. 4, 2008

(65) Prior Publication Data

US 2010/0114590 A1 May 6, 2010

(51) Int. Cl.
*G06Q 10/00* (2012.01)
*G06Q 50/00* (2012.01)
(52) U.S. Cl. .............................. 705/2; 705/3
(58) Field of Classification Search ............. 705/2–3
See application file for complete search history.

(56) References Cited

U.S. PATENT DOCUMENTS

| | | | | |
|---|---|---|---|---|
| 5,826,237 | A * | 10/1998 | Macrae et al. | 705/2 |
| 2007/0203744 | A1* | 8/2007 | Scholl | 705/2 |
| 2009/0132586 | A1* | 5/2009 | Napora et al. | 707/104.1 |

FOREIGN PATENT DOCUMENTS

WO 03025703 A1 3/2003

OTHER PUBLICATIONS

Non-final Office Action mailed Dec. 7, 2010 in U.S. Appl. No. 12/264,729.
Interview Summary mailed Jun. 9, 2011 in U.S. Appl. No. 12/264,729.
Notice of Allowance mailed Aug. 19, 2011 in U.S. Appl. No. 12/264,729, 21 pages.
Non-Final Office Action mailed Aug. 5, 2011 in U.S. Appl. No. 12/264,701, 95 pages.

* cited by examiner

*Primary Examiner* — Luke Gilligan
*Assistant Examiner* — Joseph Burgess
(74) *Attorney, Agent, or Firm* — Shook Hardy & Bacon, LLP

(57) ABSTRACT

Computerized methods and systems for permitting clinicians and other healthcare providers to designate performance locations for clinical orders having one or more phases associated therewith, and for presenting order catalog content that is flexed based upon the designated performance location for the clinical order are provided. Further provided are computerized methods and systems for permitting clinicians and other healthcare providers to designate a performance location for each phase of a multi-phase clinical order, and for presenting order catalog content for each phase that is flexed based upon the designated performance location for the phase. Systems and methods for providing control of plan and phase initiation based at least upon a location associated with the chart encounter are also provided.

25 Claims, 14 Drawing Sheets

DOE, JOHN – ADD PLAN

PLAN CATALOG
PERSONAL PLANS
PROBLEMS
  OSTEOGENIC SARCOMA (1)
DIAGNOSES

810

SEARCH MODE: KEYWORD 822  824
TOTAL                    SEARCH   AT LOCATION: 818
TYPE:  816

☐ TOTAL HIP REPLACEMENT CARE PLAN
☐ TOTAL HIP REPLACEMENT INTERDISCIPLINARY PLAN
  TOTAL HIP REPLACEMENT STANFORD
  TOTAL KNEE PATHWAY – PREOP & REHAB
  TOTAL KNEE REPLACEMENT – PREOPERATIVE (EK)

| | |
|---|---|
| DOE, JOHN | |

| FLOWSHEET | DIRECT CHARTING | NOTES | BROWSER | ORDERS | I/O | TO DO | MAR |

POWER ORDERS

AT LOCATION: XYZ CLINIC ▼  —818    TYPE: CURRENT VISIT ▼  —816

| VIEW | | |
|---|---|---|
| ORDERS FOR SIGNATURE | | |
| ⊟ PLANS 810 | INITIATE | TOTAL KNEE PATHWAY – PREOP & REHAB, PRE ADMISSION EVAL (PLANNED PENDING)  —820 |
| ⋯DOCUMENT IN PLAN | | |
| ⊞ CARE TEAM | | ✍ SIGN NOW |
| ⊟ TOTAL KNEE PATHWAY – PREOP & REHAB | | |
| ⋯PREADMISSION EVAL (PLANNED PENDING) | ⊟ NURSING ORDERS | |
| ⋯PRE OP DAY (PLANNED PENDING) | ☐ 📄 ADULT: ADMISSION HISTORY | ONCE |
| ⋯POST OP DAY OF SURGERY (PLANNED PENDING) | ☐ 📄 PREPROCEDURE EDUCATION | ONCE |
| ⋯POST OP DAY 1 (PLANNED PENDING) | ☐ 📄 CONSENT FOR SURGERY | ONCE |
| ⋯POST OP DAY 2 (PLANNED PENDING) | ⊟ LABORATORY | |
| ⋯POST OP DAY 3 REHAB TRANSFER (PLANNED PENDING) | ☐ 📄 CBC | BLOOD, COLLECTED |
| ⋯POST OP DAY 3 CLINICAL REHAB (PLANNED PENDING) | ☐ 📄 BMP | BLOOD, COLLECTED |
| ⋯POST OP PHASE 1 REHABILITATION (PLANNED PENDING) | ⊟ DIAGNOSTIC TEST | |
| | ☐ 📄 EKG | ONCE |
| | ☐ 📄 XR CHEST 1 VIEW | ROUTINE, REASON: OP |
| | ⊟ ORDERSETS | |
| | ☐ 📄 TYPE AND CROSS | |

DOE, JOHN

| FLOWSHEET | DIRECT CHARTING | NOTES | BROWSER | ORDERS | I/O | TO DO | MAR |

POWER ORDERS

AT LOCATION: HOSPITAL X ▼    TYPE: FUTURE VISIT ▼    ☐ SIGN NOW

VIEW

- ORDERS FOR SIGNATURE
- PLANS
  - DOCUMENT IN PLAN    810
  - CARE TEAM
  - TOTAL KNEE PATHWAY – PREOP & REHAB
    - PREADMISSION EVAL (PLANNED PENDING)
    - PRE OP DAY (PLANNED PENDING)
    - POST OP DAY OF SURGERY (PLANNED PENDING)
    - POST OP DAY 1 (PLANNED PENDING)
    - POST OP DAY 2 (PLANNED PENDING)
    - POST OP DAY 3 REHAB TRANSFER (PLANNED PENDING)
    - POST OP DAY 3 CLINICAL REHAB (PLANNED PENDING)
    - POST OP PHASE 1 REHABILITATION (PLANNED PENDING)

820

INITIATE    TOTAL KNEE PATHWAY – PREOP & REHAB, PRE ADMISSION EVAL (PLANNED PENDING)

- VITAL SIGNS
  - ☐ ☑ VITAL SIGNS — ONCE
  - ☐ ☑ PULSE OXIMENTRY — ONCE
- DIET
  - ☐ ☑ NPO — AFTER MIDNIGHT
- NURSING ORDERS
  - ☐ ◎ TEMPERATURE ORAL – LESS THAN 37.8 DEGC — DURING PHASE
  - ☐ ◎ OXYGEN SATURATION - GREATER THAN OR EQUAL 95% — DURING PHASE
- IV SOLUTIONS
  - ☐ ☑ DESTROSE 5% IN LACTATED FINGERS INTRAVENOUS — 75 mL/HR. IV, 1000

ORDERING CLINICAL ORDERS ASSOCIATED WITH FUTURE EVENTS

CROSS-REFERENCE TO RELATED APPLICATIONS

This application is related by subject matter to the invention disclosed in the commonly assigned applications U.S. application Ser. No. 12/264,729, entitled "Presenting Multi-Phase Clinical Order Content Based Upon a Designated Performance Location", and U.S. application Ser. No. 12/264,701, entitled "User Interface for Presenting Clinical Order Content Based Upon Designated Performance Location", each of which is filed on even date herewith and each of which is hereby incorporated by reference herein in its entirety.

BACKGROUND

Clinical orders are requests placed by clinical or healthcare providers for, e.g., procedures, medications, laboratory tests, evaluations, treatments, and nursing tasks to be done for a patient. In a non-electronic clinical order system, clinical orders from different categories in one healthcare plan (such as medications, labs, diagnostic tests, and nursing orders) are generally documented on a single piece of paper. A healthcare plan includes multiple orders for treatment for a particular problem or ailment. For example, a healthcare plan for a cancer patient may include multiple medication orders and laboratory testing orders. Once these orders are reviewed by a healthcare provider, the necessary orders for different categories are forwarded to the correct location to be completed or filled. For example, if one order includes a medication, a medication paper order may be sent to the pharmacy to be filled. If one of the orders in the healthcare plan is for a laboratory test, a paper laboratory requisition form may be sent to the laboratory. In the paper healthcare ordering system, it is typically possible to go back to the original paper order set containing all of the orders for the healthcare plan. An example of a healthcare plan or procedure would be chemotherapy protocol that includes multiple orders for medications, laboratory tests, and diagnostic tests. Another example would be an arthroscopic surgical protocol that includes a pre-operative consultation, a surgical procedure, post-operative care, and physical therapy.

In an electronic healthcare order environment, if a set of orders is placed for a healthcare plan, once the orders have been reviewed, they are electronically dispersed to the appropriate location, such as the pharmacy or laboratory application. U.S. patent application Ser. Nos. 11/022,540, 11/020,489, and 11/021,509 (each of which is hereby incorporated by reference herein in its entirety) describe methods and systems for creating and maintaining associations among the orders in a healthcare plan in a computerized environment such that the associations may be accessed and viewed after one or more of the orders is distributed to the proper application to be filled.

Often times a clinical order (or set of clinical orders) will set forth a healthcare plan having components which span multiple phases. For instance, a healthcare plan for a chemotherapy protocol may specify that a particular medication is to be given in a specified dosage on three separate days, e.g., Day 1, Day 8, and Day 15. In this instance, each day may be viewed as a separate phase. Phases, however, are not limited to units of time. In simple terms, a phase is merely a plan and, accordingly, may be a unit of time, a diagnostic grouping, or any other sub-plan within a healthcare plan. In another example, a healthcare plan for an arthroscopic surgical protocol may specify that a pre-operative consultation, a surgical procedure, post-operative care, and physical therapy are to occur for a particular patient. In this instance, each of the pre-operative consultation, the surgical procedure, the post-operative care and the physical therapy are different phases of the clinical order for the arthroscopic surgical protocol.

Typically, in an electronic healthcare order environment, when a clinical order (or set of orders) spans multiple phases, each component of each phase appears to a user as a separate order. More importantly, each component of each phase appears to the electronic environment as a separate order. This means that each component of each phase must be entered into the electronic system separately and any modification to a particular component must be entered for that component in each of the phases in which it may appear. For instance, in the above chemotherapy protocol example, if it is desired to modify the dosage of the medication that is to be given to the patient on each of Days 1, 8 and 15, such modification must be separately entered for each of the three phases. Such duplicate entering is not only inefficient but increases the possibility of human error.

U.S. patent application Ser. Nos. 11/359,011, 11/359,012, and 11/359,013 (each of which is hereby incorporated by reference herein in its entirety) describe methods and systems for associating components which span multiple phases of a healthcare plan and permitting modification of components thereof to be applied to all components associated therewith. In this way, modifications may be entered one time instead of once for each phase to which they apply.

Utilizing a plan-based system such as that described in U.S. patent application Ser. Nos. 11/359,011, 11/359,012 and 11/359,013, healthcare plans spanning multiple phases may be ordered by a clinician or other healthcare provider as a unit. That is, a clinician or other healthcare provider may order a chemotherapy or arthroscopic surgery protocol for a particular patient, and each phase associated with the ordered protocol will be ordered. However, such multi-phase healthcare plans may only be ordered if the plan is capable of being performed at the same location or facility. For instance, it may be possible for a clinician to place an order for a chemotherapy protocol as it is likely that each phase of the chemotherapy protocol is going to be performed at the same location, e.g., the hospital or outpatient treatment facility. With respect to the arthroscopic surgery protocol, however, it is likely that some of the phases are not going to be performed at the same location. For instance, the surgical procedure and post-operative care are likely to be performed at a hospital while the physical therapy is likely to be performed at an outpatient physical therapy clinic. Thus, in the arthroscopic surgery protocol example, since all phases are not to be performed at the same location, ordering of the protocol as a single unit by placing a single clinical order is not possible.

Generally, the primary reason that a healthcare plan having multiple phases that are not all to be performed at the same location cannot be ordered by placing a single clinical order is because of the order catalog options made available to the ordering clinician or other healthcare provider. That is, when viewing the order catalog from which to select plans to be performed, the content of the order catalog that is made available to the ordering clinician includes only those plans which can be performed in association with a particular location—generally the location of the chart encounter (that is, the encounter the clinician or other healthcare provider has currently selected within the patient's chart). Thus, if a clinician is currently engaged with a chart encounter associated with a hospital, only plans that can be performed in their entirety at the hospital will be made available to the clinician for selection. In this way, not only are available plans limited to those plans which can be performed in their entirety at a single location, the single location at which they can be performed is the location of the chart encounter. Thus, healthcare plans that include multiple phases, wherein at least two of the phases are to be performed at differing locations with respect to one another, must be ordered as separate orders rather than as a single unit. Further, even plans having multiple phases, each of which is to be performed at the same location, cannot be ordered in association with a chart encounter as such plans will not be made available to the clinician or other healthcare provider for selection.

BRIEF SUMMARY

Embodiments of the present invention relate to computer-readable media having computer-executable instructions embodied thereon for performing methods, in a clinical computing environment, for permitting ordering of clinical orders to be associated with future encounters. In one embodiment, the method includes receiving, in association with a chart encounter associated with a first location, an indication that a user desires to place a clinical order, the clinical order having one or more phases associated therewith, each of the one or more phases to be performed at the same location, and each of the one or more phases having a plurality of orders associated therewith. The method further includes receiving a performance location designation to be associated with the clinical order, and presenting at least one selectable clinical order option representing an orderable clinical order having one or more phases associated therewith, each of the phases being capable of being performed at the designated performance location, and each of the phases having a plurality of orders associated therewith. The method in accordance with this embodiment may further include receiving a selection of one of the selectable clinical order options and presenting content associated with the orderable clinical order represented by the selected clinical order option.

Further embodiments of the present invention relate to computer-readable media having computer-executable instructions embodied thereon for performing a method in a clinical computing environment, for permitting ordering of clinical orders to be associated with a future encounter. In one embodiment, the method includes receiving, in association with a chart encounter associated with a first location, an indication that a user desires to place a clinical order, the clinical order having a plurality of phases associated therewith, each of the plurality of phases to be performed at the same location. The method further includes receiving a performance location designation to be associated with the clinical order, and presenting at least one selectable clinical order option, each selectable clinical order option representing an orderable clinical order having a plurality of phases associated therewith, each of the plurality of phases being capable of being performed at the designated performance location. The method in accordance with this embodiment may further include receiving a selection of one of the selectable clinical order options and presenting content associated with the orderable clinical order represented by the selected clinical order option.

Embodiments of the present invention further relate to methods, in a clinical computing environment, for permitting ordering of clinical orders to be associated with future encounters. The method includes receiving, in association with a chart encounter associated with a first location, an indication that a user desires to place a clinical order, the clinical order having one or more phases associated therewith, each of the phases to be performed at the same location.

The method further includes receiving a grouped-performance-location designation to be associated with the clinical order and presenting at least one selectable clinical order option, each clinical order option representing an orderable clinical order each phase of which is capable of being performed at one or more of a plurality of locations associated with the grouped-performance-location designation. The method in accordance with this embodiment may further include receiving a selection of one of the selectable clinical order options and presenting each of the plurality of locations at which the selected clinical order option is capable of being performed, receiving a selection of one of the presented locations and presenting content associated with the orderable clinical order represented by the selected clinical order option flexed based upon the selected location.

Still further, embodiments of the present invention relate to systems, in a clinical computing environment, for permitting ordering of clinical orders to be associated with a future encounter. In one embodiment, the system includes an order indication receiving component, an encounter-type receiving component, a location receiving component and a presenting component. The order indication receiving component receives, in association with a chart encounter associated with a first location, an indication that a user desires to place a clinical order, the clinical order having one or more phases associated therewith, each of the phases to be performed at the same location. The encounter-type receiving component receives an indication that the clinical encounter is to be performed in association with a future encounter. The location receiving component receives a performance location designation to be associated with the clinical order. The presenting component presents at least one selectable clinical order option, each option representing an orderable clinical order having one or more phases associated therewith, each of the phases being capable of being performed at the designated performance location. The system in accordance with this embodiment may further include a selection receiving component that receives a selection of one of the clinical order options and the presenting component may further present content associated with the orderable clinical order represented by the selected clinical order option.

Embodiments of the present invention further relate to computer-readable media having computer-executable instructions embodied thereon for performing methods, in a clinical computing environment, for presenting content associated with multi-phase clinical orders based upon a designated performance location. In one embodiment, the method includes receiving, in association with a chart encounter associated with a first location, selection of a multi-phase clinical order; for each of the phases of the multi-phase clinical order, receiving a performance location designation representing a location at which the associated phase is to be performed, the performance location designations for at least two of the phases of the multi-phase clinical order differing from one another; and presenting content associated with at least one phase of the multi-phase clinical order, the presented content being based upon the selected performance location associated with the at least one phase.

Additionally, embodiments of the present invention relate to methods, in a clinical computing environment, for presenting content associated with multi-phase clinical orders based upon designated performance locations. In one embodiment, the method includes receiving, in association with a chart encounter associated with a first performance location, an indication that a user desires to place a multi-phase clinical order; presenting at least one selectable multi-phase clinical order option, each presented selectable multi-phase clinical order option representing a multi-phase clinical order having at least one phase that is capable of being performed at the first performance location; receiving a selection of one of the at least one selectable multi-phase clinical order options; presenting a phase indicator for each of the phases associated with the selected multi-phase clinical order option; receiving a selection of one of the presented phase indicators; receiving a performance location designation for a phase of the multi-phase clinical order that is associated with the selected phase indicator; and presenting content associated with the phase of the multi-phase clinical order that is associated with the selected phase indicators, the presented content being based upon the received performance location designation.

Embodiments of the present invention further relate to systems, in a clinical computing environment, for presenting content associated with multi-phase clinical orders based upon designated performance locations. In one embodiment, the system includes an order indication receiving component, a presenting component, a selection receiving component and a location receiving component. The order indication receiving component receives, in association with a chart encounter associated with a first performance location, an indication that a user desires to place a clinical order, the clinical order having multiple phases associated therewith. The presenting component presents at least one selectable clinical order option, each selectable clinical order option representing a multi-phase clinical order having at least one phase that is capable of being performed at the first performance location, and a phase indicator for each of the phases associated with a selected one of the clinical order options. The selection receiving component receives a selection of one of the clinical order options and a selection of one of the phase indicators associated with the selected clinical order option. The location receiving component receives a performance location designation associated with a phase of the multi-phase clinical order that is associated with the selected phase indicator. If desired, the system may further include one or more of an encounter-type receiving component that receives an indication that the clinical order is to be performed in association with a future encounter, an individualization component that receives detail-level individualization information for the phase of the multi-phase clinical order that is associated with the selected phase indicator, a location-association determining component that determines that the phase of the multi-phase clinical order that is associated with the selected phase indicator is locationally-associated with another phase of the multi-phase clinical order, an associating component that automatically associates the designated performance location with the other phase, an initiation determining component that determines whether the phase of the multi-phase clinical order that is associated with the selected phase indicator is capable of being initiated in association with the chart encounter, and an initiating component that initiates the phase of the multi-phase clinical order that is associated with the selected phase indicator upon determination that the phase is capable of being initiated in association with the chart encounter.

Still further, embodiments of the present invention relate to user interfaces embodied on at least one computer-readable medium the user interface for presenting content associated with clinical orders based upon designated performance location. In one embodiment, the user interface includes a location-specification display area that receives and displays a designated performance location to be associated with a clinical order, and a clinical order information display area that presents content associated with the clinical order, the information being based upon the designated performance location.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein:

FIG. 9 is an illustrative screen display of an exemplary user interface, in accordance with an embodiment of the present invention, wherein location and encounter-type designations are not necessarily designated before presentation of appropriate clinical order content;

FIG. 10 is an illustrative screen display of an exemplary user interface, in accordance with an embodiment of the present invention, that may be utilized to receive location and encounter-type designations and present appropriate phase-level content based upon such designations;

FIG. 12 is an illustrative screen display of an exemplary user interface, in accordance with an embodiment of the present invention, that may be utilized to receive location and encounter-type designations; and FIG. 13 is an illustrative screen display of an exemplary user interface, in accordance with an embodiment of the present invention, displaying an indication that initiation of a selected phase is not permitted.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for permitting clinicians and other healthcare providers to designate performance locations for clinical orders having one or more phases associated therewith, and for presenting order catalog content that is flexed based upon the designated performance location for the clinical order. Embodiments of the present invention further provide computerized methods and systems for permitting clinicians and other healthcare providers to designate a performance location for each phase of a multi-phase clinical order, and for presenting order catalog content for each phase that is flexed based upon the designated performance location for the phase. Embodiments of the present invention additionally provide control of plan and phase initiation based at least upon a location associated with the chart encounter. An exemplary operating environment for the present invention is described below.

Figure 1:
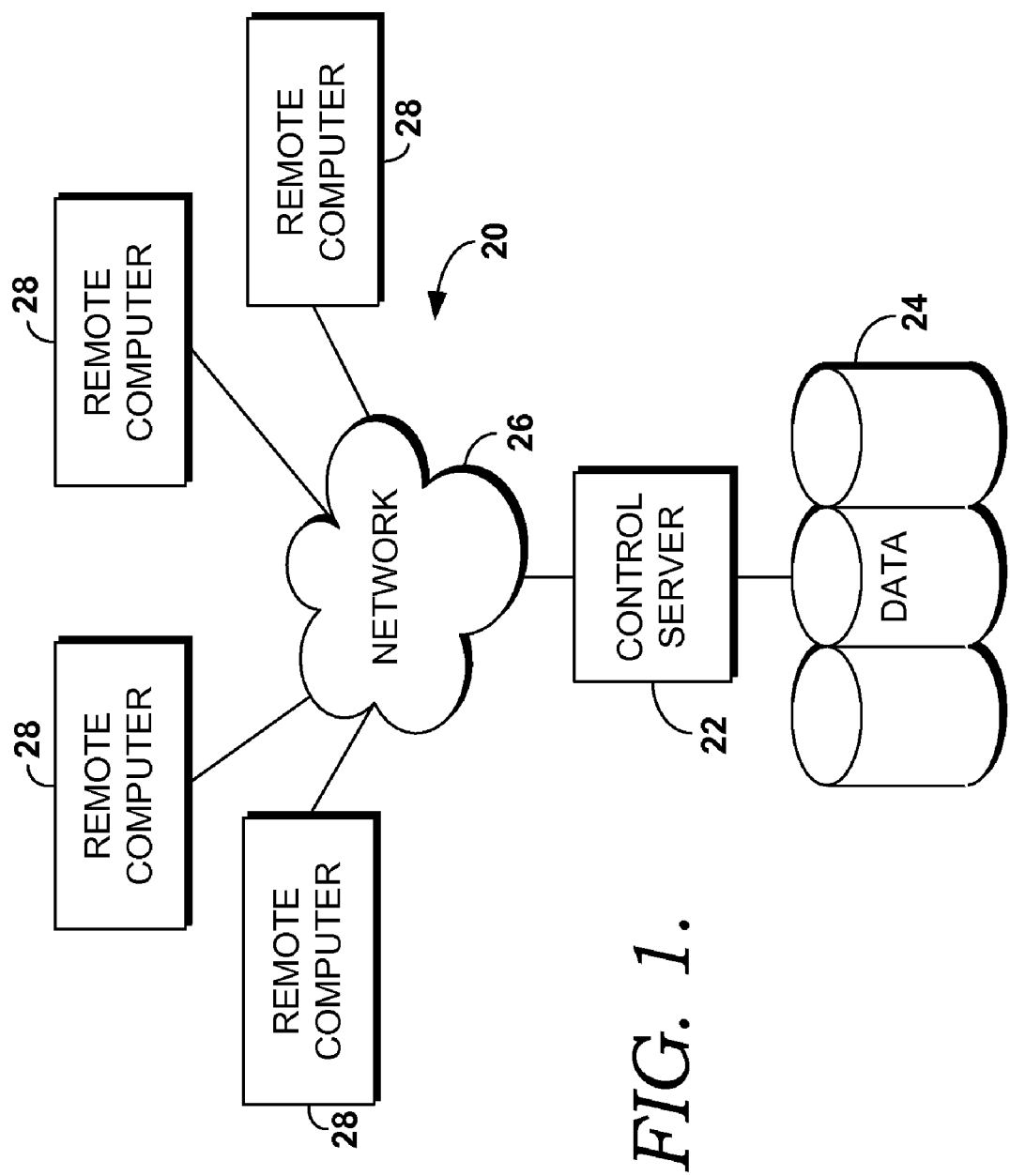
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may comprise computer storage media. Computer storage media may include, without limitation, volatile and nonvolatile media, as well as removable and non-removable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network.

The remote computers 28 may be personal computers, servers, routers, network PCs, peer devices, other common network nodes, or the like, and may include some or all of the elements described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare-related orders, particularly, molecular diagnostic orders. As contemplated by the language above, the methods and systems of embodiments of the present invention may also be implemented on a stand-alone desktop, personal computer, or any other computing device used in a healthcare environment or any of a number of other locations.

Figure 2:
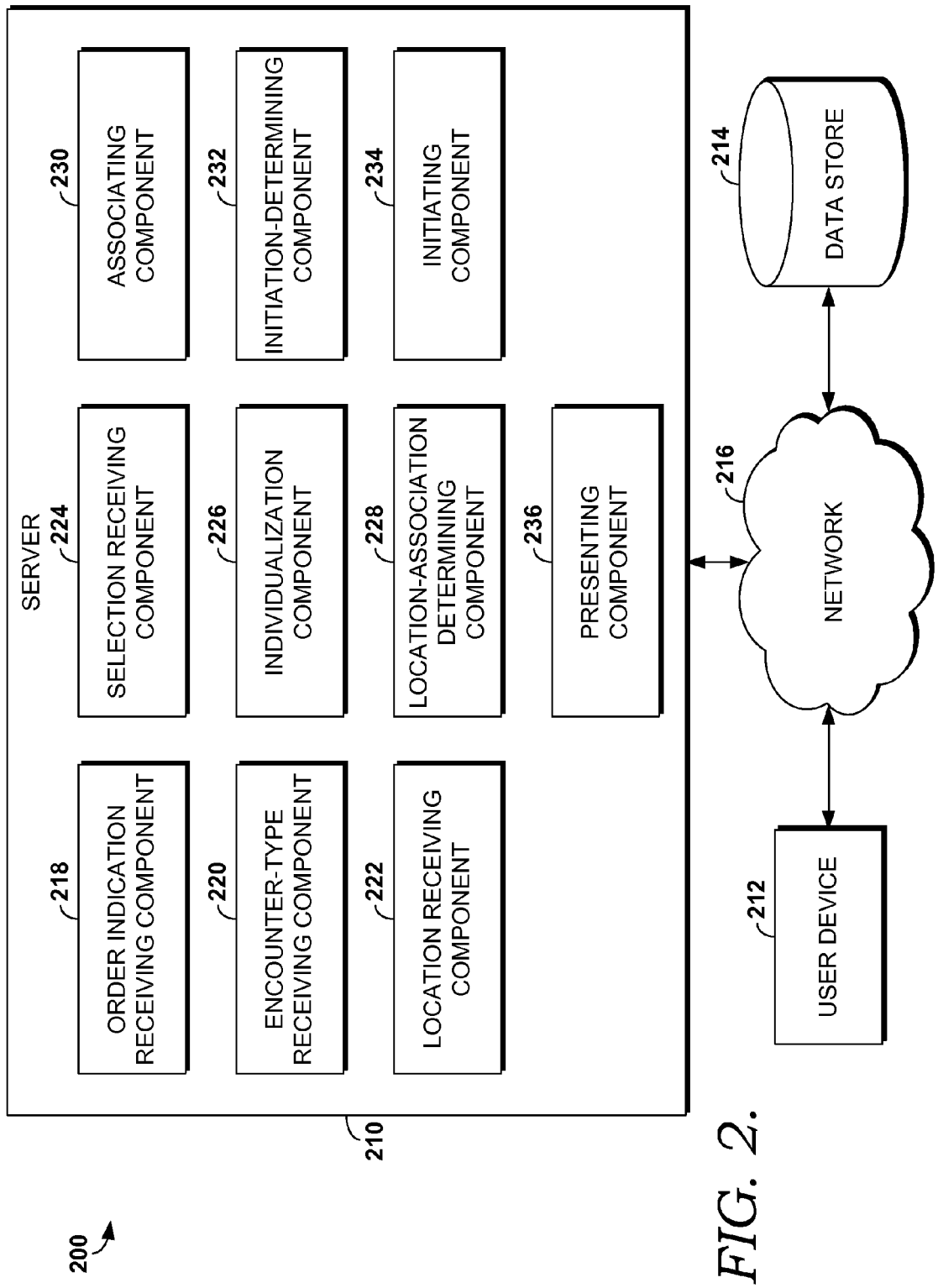
FIG. 2 is a block diagram of an exemplary computing system suitable for implementing embodiments of the present invention.

As previously mentioned, embodiments of the present invention relate to computerized methods and systems for permitting clinicians and other healthcare providers to designate performance locations for clinical orders having one or more phases associated therewith, and for presenting order catalog content that is flexed based upon the designated performance location for the clinical order. Embodiments of the present invention further relate to computerized methods and systems for permitting clinicians and other healthcare providers to designate a performance location for each phase of a multi-phase clinical order, and for presenting order catalog content for each phase that is flexed based upon the designated performance location for the phase. Additionally, embodiments of the present invention relate to control of plan and phase initiation based at least upon a location associated with the chart encounter. With reference to FIG. 2, an exemplary computing system suitable for implementing embodiments of the present invention is illustrated and designated generally as reference numeral 200. System 200 includes a server 210, a user device 212, and a data store 214, all in communication with one another through a network 216. The network 216 may include, without limitation, one or more local area networks (LANs) and/or wide area networks (WANs). Such networking environments are commonplace in offices, enterprise-wide computer networks, intranets, and the Internet. Accordingly, the network 216 is not further described herein.

The data store 214 is configured to store information associated with at least one clinical order for a patient, the clinical order having one or more phases associated therewith. (The terms "individual", "person", and "patient" are used interchangeably herein and are not meant to limit the nature of the referenced individual in any way. Rather the methods and systems described herein are equally applicable, for instance, in a veterinary setting. Further, use of the term "patient" is not meant to imply any particular relationship between the individual and those inputting, ordering and/or individualizing the clinical order.) In various embodiments, such information may include, without limitation, a clinical order designation, a location to be associated with a clinical order, a location to be associated with a particular phase of the clinical order, plan level details related to the clinical order (standard or individualized), order-level details related to a particular phase of the clinical order (standard or individualized), and the like. In embodiments, the data store 214 is configured to be searchable for one or more clinical orders, phases and/or plan/order details stored in association therewith. It will be understood and appreciated by those of ordinary skill in the art that the information stored in the data store 214 may be configurable and may include any information relevant to a clinical order and/or a patient associated therewith. The content and volume of such information are not intended to limit the scope of embodiments of the present invention in any way. Further, though illustrated as a single, independent component, the data store 214 may, in fact, be a plurality of data stores, for instance, a database cluster, portions of which may reside on the server 210, the user device 212, another external computing device (not shown) and/or any combination thereof.

The server 210 includes various components and is configured to operate utilizing at least a portion of the information stored in the data store 214. The illustrated server 210 includes an order indication receiving component 218, an encounter-type receiving component 220, a location receiving component 222, a selection receiving component 224, an individualization component 226, a location-association determining component 228, an associating component 230, an initiation-determining component 232, an initiating component 234, and a presenting component 236. It will be understood and appreciated by those of ordinary skill in the art that other components not shown may also be included with the system 200. Further, additional components not shown may also be included within any of the server 210, the user device 212, the data store 214, and/or another external computing device (not shown). Any and all such variations are contemplated to be within the scope of embodiments hereof.

Figure 5:
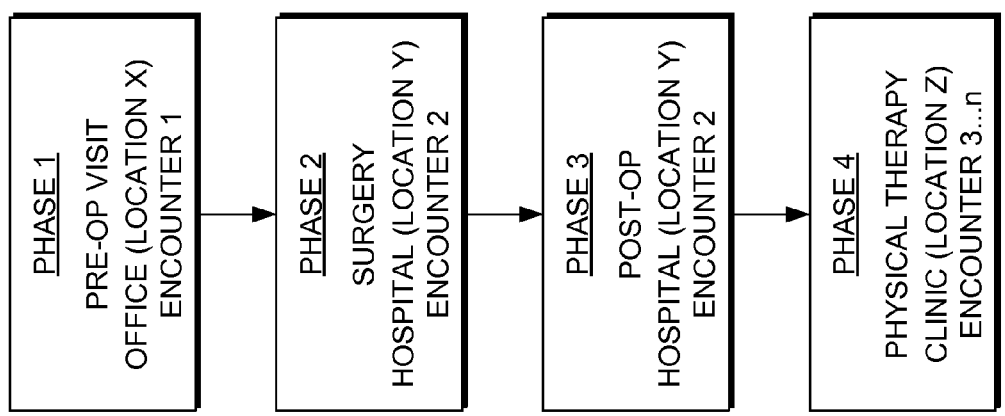
FIG. 5 is a schematic diagram of an exemplary multi-phase clinical order having phases to be performed at differing locations, in accordance with an embodiment of the present invention.

The order-indication receiving component 218 is configured to receive, in association with a chart encounter associated with a first performance location (i.e., the encounter the user has selected within the patient's electronic record at the current time and at the current performance location), an indication that the user desires to place a clinical order. In embodiments, the clinical order includes one or more phases associated therewith. For instance, a healthcare plan containing a chemotherapy protocol for a patient may specify that a particular medication, cyclophosphamide, is to be administered to the patient in a normalized dose of 500 mg/m² on each of Day 1, Day 8, and Day 15 of treatment. In this instance, each of Day 1, Day 8 an Day 15 are different phases of the clinical order for the chemotherapy protocol. In another example, a healthcare plan containing an arthroscopic surgical protocol for a patient may specify that a pre-operative consultation, a surgical procedure, post-operative care, and physical therapy are to occur for a particular patient. In this instance, each of the pre-operative consultation, the surgical procedure, the post-operative care and the physical therapy are different phases of the clinical order for the arthroscopic surgical protocol. (It should be noted that this latter example is illustrated in FIG. 5 and more fully described herein below.)

Figure 8:
FIG. 8 is an illustrative screen display of an exemplary user interface, in accordance with an embodiment of the present invention, that may be utilized to receive location and encounter-type designations and present appropriate clinical order content based upon such designations.
Figure 11:
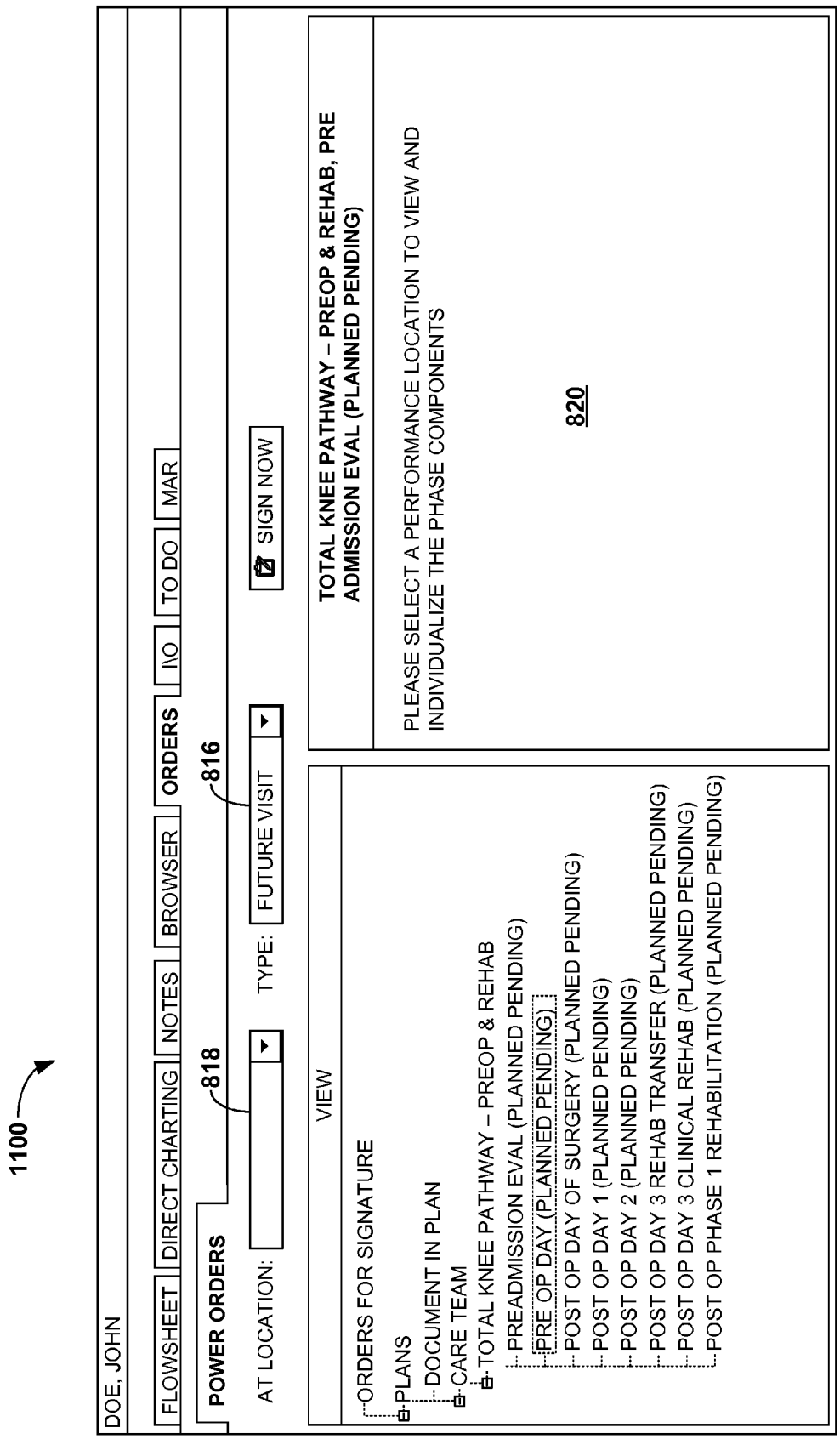
FIG. 11 is an illustrative screen display of an exemplary user interface, in accordance with an embodiment of the present invention, indicating that a performance location is to be input or selected prior to display of appropriate phase-level content.

Referring to FIG. 8, a screen display of an exemplary user interface 800 that may be utilized for receiving an indication that a user desires to place a clinical order is illustrated. (It is noted that the user interface 800 of FIG. 8 is configured for designation of a performance location on a plan level (or an initial filtering stage, as more fully described below). Designation of a performance location on a phase level is more fully described below with reference to FIGS. 10-14.) In the illustrated user interface 800, a user may evidence a desire to place a clinical order by selecting the "PLAN CATALOG" indicator 812 or the "PERSONAL PLANS" indicator 814 from the presented selection options display area 810. The "PLAN CATALOG" indicator 812 is shown as selected in the illustrated user interface 800. Upon user selection of the "PLAN CATALOG" indicator 812, an indication that the user desires to place a clinical order selected from the plan catalog may be received by the order-indication receiving component 218 of FIG. 2.

Returning to FIG. 2, the encounter-type receiving component 220 is configured to receive an indication that a clinical order is to be performed in association with either the chart (or current) encounter or a future encounter, that is, an encounter within the patient's electronic record associated with a future time of performance. If desired, the encounter-type receiving component 220 further may be configured to receive an indication of encounter-type based upon a criterion other than time of performance. For instance, the encounter-type receiving component 220 may be configured to receive an indication that the encounter for which placement of a clinical order is being initiated is an inpatient encounter or outpatient encounter. Any and all such variations are contemplated to be within the scope hereof.

With reference again to the screen display of FIG. 8, a user may specify the type of encounter for which it is desired to place a clinical order by inputting, or selecting from a pre-defined list of options, an encounter-type in encounter-type options display area 816. If desired, default content may appear in encounter-type options display area 816 upon selection of an indicator (e.g., the "PLAN CATALOG" indicator) from the selection options display area 810. In the illustrated user interface 800, upon selection of the "FUTURE VISIT" encounter-type in the encounter-type options display area 816, and indication that the user desires to place a clinical order for a future visit may be received by the encounter-type receiving component 220 of FIG. 2.

Returning to FIG. 2, the location receiving component 222 is configured to receive a performance location designation to be associated with a clinical order being placed by the user. The designated performance location may be the location associated with the chart encounter or a performance location differing from the location of the chart encounter. In one embodiment, if an indication has been received (e.g., utilizing encounter-type receiving component 220) that the user desires the clinical order being placed to be performed in association with the chart encounter (as opposed to a future encounter), the designated performance location will default to the location associated with the chart encounter and specification by the user of a desired performance location will not be necessary.

In embodiments, the designated performance location may be a grouped-performance location. A grouped-performance location designation is a location designation that represents a plurality of locations. For instance, a grouped-performance location of "all" would cause flexing of the content associated with a selected clinical order or phase of a clinical order based upon all of the locations at which the particular clinical order or phase is capable of being performed. In such embodiments, subsequent selection of a particular location within the grouping is eventually required before ordering of the clinical order or phase is permitted.

Turning again to the screen display of FIG. 8, a user may specify the location at which it is desired for the clinical order being placed to be performed by inputting, or selecting from a pre-defined list of options, a performance location in location-specification display area 818. In embodiments, a pre-defined listing of allowable performance locations based, for instance, on the identity of the user placing the clinical order, is made available for selection in association with the location-specification display area 818.

It will be understood and appreciated by persons having ordinary skill in the art that input and receipt of both an encounter-type and a performance location designation may not be necessary. For instance, if a performance location is designated as other than the location of the chart encounter, clearly the clinical order being placed is intended for a future visit and specific input and receipt of an encounter-type is not necessary.

Returning to FIG. 2, upon receipt of a performance location designation and/or encounter-type, content from the plan catalog (or other plan selection database) is flexed and presented by presenting component 236. That is, based upon the information received by one or both of the encounter-type receiving component 220 and the location receiving component 222, plans that are available to the user for selection are presented. As will be understood by those of ordinary skill in the art, such presentation by the presenting component 236 will typically be implemented via the presenting component 236 accessing user, encounter-type and/or location based plan information from the data store 214 (through the network 216), and transmitting such accessed plan information through the network 216 to the user device 212 where it is presented to the user. Such accessing and transmitting of information are well known to those of ordinary skill in the art and, accordingly, are not further described herein. The presenting component 236 and additional functionality that may be associated therewith is more fully described below.

With reference back to FIG. 8, in the illustrated embodiment, the accessed and transmitted plan information is displayed in the clinical order information display area 820 of user interface 800 in the form of selectable clinical order options. Generally, due to the volume of plan information available to a user, further filtering of the selectable clinical order options to be displayed based upon keyword will be desired. Thus, a user may input into the keyword search field 822, one or more keywords that are to be included in all returned selectable clinical order options. In the illustrated embodiment, the user has filtered the clinical order options based upon the keyword "TOTAL" and all selectable clinical order options returned and presented in the clinical order information display area 820 contain the word "TOTAL" therein. Subsequent to input of the keyword, the "SEARCH" button 824 may be selected to initiate searching of a data store (e.g., data store 214 of FIG. 2) for the appropriate information.

With reference to FIG. 9, an screen display of another embodiment of an exemplary user interface 900 that may be utilized in similar fashion to that described above with reference to FIG. 8 is illustrated and designated generally as reference numeral 900. In the illustrated embodiment, the user has specified that the clinical order options be filtered only based upon keyword and has not designated either a performance location or encounter-type. Accordingly, both the encounter-type options display area 816 and the location specification display area 818 have no content displayed therein and all selectable clinical order options displayed in the clinical order information display area 820 are automatically filtered based upon the location of the chart encounter. In an alternative embodiment (not shown), the content of the encounter-type options display area 816 and/or the location specification display area 818 may display the state of default (e.g., current encounter and location associated with the chart encounter, respectively). Any an all such variations are contemplated to be within the scope of embodiments of the present invention.

Returning now to FIG. 2, the selection receiving component 224 is configured to receive a selection of a selectable clinical order option. With reference to FIG. 10, a screen display of an exemplary user interface 1000 that may be displayed subsequent to user selection of a selectable clinical order option displayed in the clinical order information display area 820 of FIG. 8 is illustrated and designated generally as reference numeral 1000. In the illustrated embodiment, the user has selected the clinical order option "TOTAL KNEE PATHWAY—PREOP & REHAB" from the clinical order information display area 820 of FIG. 8. As illustrated in FIG. 10, the content of the selection options display area 810 and the clinical order information display area 820 has flexed based upon the received clinical order selection. Thus, upon the user selecting the "TOTAL KNEE PATHWAY—PREOP & REHAB" clinical order option, such selection was received, e.g., by selection receiving component 224 of FIG. 2, and appropriately flexed content based upon the selected clinical order option was presented (e.g., utilizing presenting component 236 of FIG. 2) in both the selection options display area 810 and clinical order information display area 820. The displayed content shown in the selection options display area 810 now lists the various phases that are included in the TOTAL KNEE PATHWAY—PREOP & REHAB healthcare plan (clinical order).

With reference to FIG. 2, the selection receiving component 224 is further configured to receive a selection of one of the phase indicators associated with a selected clinical order option. For instance, in the embodiment illustrated in FIG. 10, one of the phases (i.e., "PREADMISSION EVAL (PLANNED PENDING)") has been selected by the user in the selection options display area 810 (and received, for instance, by selection receiving component 224 of FIG. 2). Accordingly, the content of the clinical order information display area 820 includes order level details associated with the selected phase. If a particular phase had not yet been selected by the user, the clinical order information display area may display the same phase information as is illustrated in the selection options display area 810 (or a portion thereof), or the clinical order information display area 820 may have no content displayed therein. Any and all such variations are contemplated to be within the scope of embodiments of the present invention.

With continued reference to the user interface 1000 of FIG. 10, note that an encounter-type has been input, selected, or defaulted in the encounter-type options display area 816 and a performance location has been designated (via input, selection, or default) in the location-specification display area 818. The information in each of these fields 816 and 818 is now specific to the selected phase. That is, the user has indicated that the phase selected in the selection options display area 810 (i.e., "PREADMISSION EVAL (PLANNED PENDING)") is to be performed during the current visit at XYZ Clinic. In accordance with such user designations, the order details displayed in the clinical order information display area 820 are flexed. Accordingly, referring back to FIG. 2, the encounter-type receiving component 220 is further configured to receive an indication that a particular phase of a clinical order is to be performed in association with either the chart (or current) encounter or a future encounter and the location receiving component 222 is further configured to receive a performance location designation to be associated with a particular phase of the clinical order being placed by the user.

Contrast FIG. 10 with the user interface 1200 of FIG. 12. The same phase of the TOTAL KNEE PATHWAY—PREOP & REHAB multi-phase clinical order has been selected but the content displayed in the clinical order information display area 820 differs. This is due to the differing encounter type and/or performance locations designated. The contrast between these two figures illustrates the flexing of the detail-level content based upon location and/or encounter type.

With reference back to FIG. 10, as the selected phase is to be performed in association with the current visit, the location associated with the chart encounter associated with the user interface 1000 of FIG. 10 is XYZ clinic. Thus, the location displayed in the location-specification display area 818 may be a defaulted location and the order details displayed in the clinical order information display area 820 may have been automatically presented upon designation of the encounter type. If the user had instead indicated that the encounter-type was to be a future visit, user designation of a performance location would have been necessary prior to content being displayed in the clinical order information display area 820. In one embodiment, prior to user designation of a performance location in the location-specification display area 818, a message alerting the user that a performance location must be input prior to display of the order details associated with the selected phase may be presented in the clinical order information display area 820. An exemplary such embodiment is illustrated in the user interface 1100 of FIG. 11. Similarly, if the phase selected in the selection options display area 810 is not capable of being performed at the location of the chart encounter, the encounter type may default to FUTURE VISIT and the user interface 1100 of FIG. 11 may be presented. In such embodiment, the user would not be permitted to manually change the type of encounter presented in the encounter-type options display area 816.

Once clinical order information or order details associated with a particular phase are presented in the clinical order information display area 820 (e.g., FIGS. 9 or 10, respectively), individualization of the content may be implemented by the user. Accordingly, with reference back to FIG. 2, the individualization component 226 is configured to receive order-level individualization information and/or detail-level individualization information for a clinical order and/or a particular phase of a clinical order, respectively. Individualization is generally allowed as long as the specified information is capable of being implemented at the designated location. In embodiments, if a user attempts to input individualization information that is not permitted based upon the designated location, a message indicating such (not shown) may be displayed.

Often, more than one phase of a multi-phase clinical order is performed as part of a single patient encounter. For instance, a patient undergoing surgery is likely admitted to the surgical location and undergoes pre-operative preparation, surgery and post-operative care before being discharged from the surgical location. Thus, while each of pre-operative preparation, surgery and post-operative care may be different phases of a multi-phase clinical order, each of these phases is part of a single patient encounter. Accordingly, in such circumstances, a single performance location should be designated and enforced with respect to all of the locationally-associated phases. In this regard, the location-association determining component 228 is configured to determine that a particular phase of a multi-phase clinical order is locationally-associated with another phase of the multi-phase clinical order. Further, upon determination that a particular phase of the multi-phase clinical order is locationally-associated with at least one other phase of the multi-phase clinical order, the associating component 230 is configured to automatically associate (that is, without user intervention), the designated performance location specified for the particular phase with the other locationally-associated phase(s). Such association will then be enforced and any attempt by the user to alter the performance location designation associated with one of the phases will result in an error message (not shown) being displayed or a message (not shown) indicating that alteration of that particular performance location designation will result in alteration of the location of other locationally-associated phases.

In accordance with embodiments of the present invention, the fact that a clinical order having one or more phases associated therewith may be ordered does not necessarily mean that the clinical orders and/or phases may be initiated. That is, initiation of ordered clinical orders and/or phases may be limited based upon designated performance location and/or the existence of intervening phases. Generally, initiation of clinical orders and/or phases having a designated performance location that is the same as the location of the chart encounter are permitted, as long as there are no intervening orders or phases the completion of which is required prior to initiation of the clinical order or phase. In this regard, the initiation-determining component 232 is configured to determine whether a selected phase of a multi-phase clinical order is capable of being initiated in association with the chart encounter. A phase is capable of being initiated in association with the chart encounter if it is designated to be performed at the location associated with the chart encounter and all requirements regarding completion of other orders or phases prior to initiation have been met.

Figure 13:
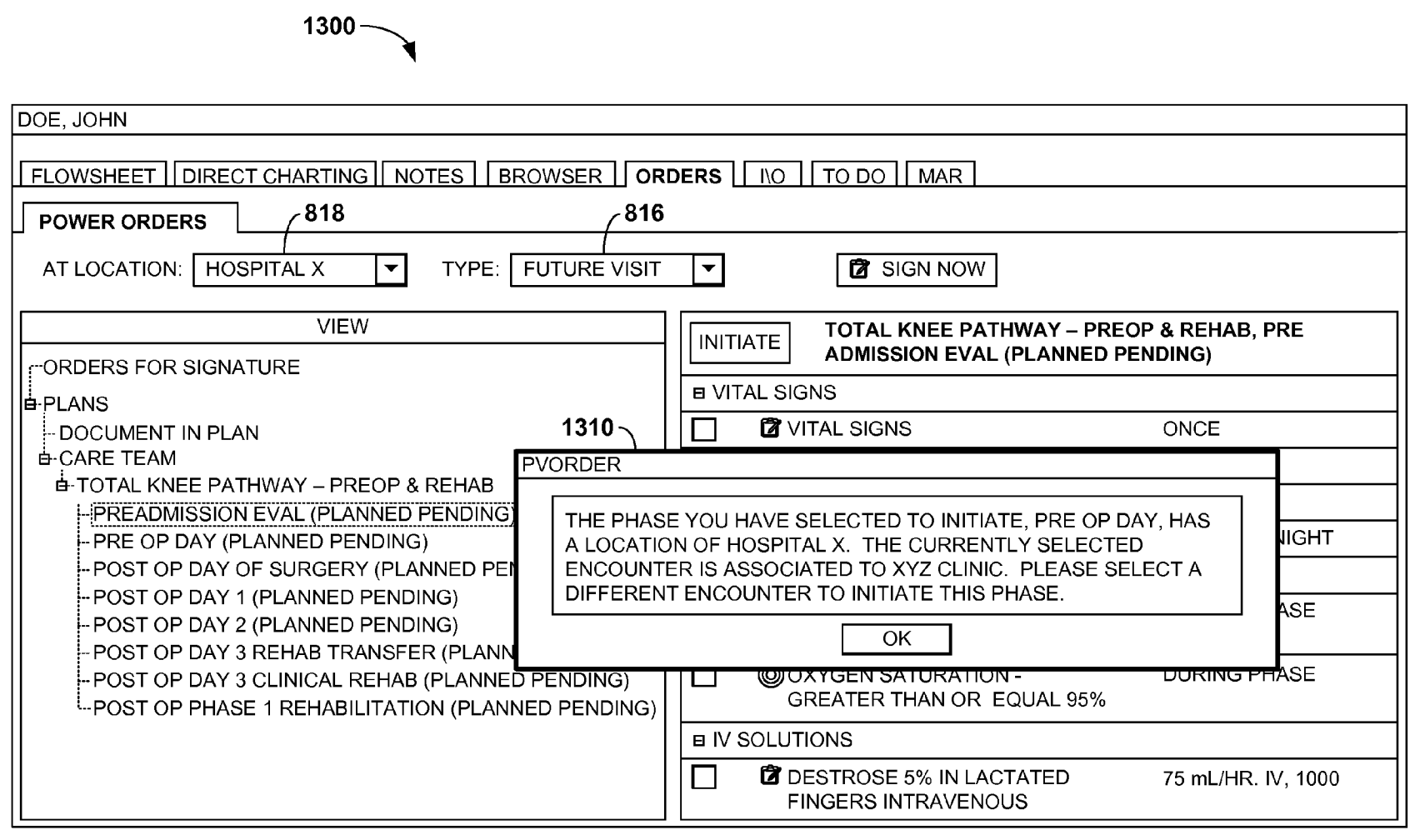

For instance, referring back to the arthroscopic surgical protocol described herein above, if the post-operative care phase and the surgical phase are to be performed at the same location (for instance, if the two phases are locationally-associated with one another), the post-operative care phase may be capable of being initiated by a user engaged in a chart encounter with the surgical phase if no requirement regarding completion of the surgical phase prior to initiation of the post-operative care phase would prevent such initiation. If, however, a user attempts to initiate a phase associated with a performance location other than the location associated with the chart encounter, or if any intervening phases are required to be completed prior to initiation of the phase, an error message may be presented to the user, e.g., utilizing presenting component 236. A screen display showing an exemplary user interface 1300 having such an error message 1310 is illustrated in FIG. 13. In response to the displayed message 1310, the user may alter either the performance location designated in the location-specification display area 818 or the encounter type designated in the encounter-type options display area 816, which would default the performance location to the location associated with the chart encounter, if initiation of the phase is still desired. If the user chooses not to alter either of the encounter-type or performance location designation, the phase may be initiated at the time of engagement of a patient encounter at Hospital X (so long as completion of all intervening phases for which completion is required have been completed).

Returning to FIG. 2, upon determining that a phase is capable of being initiated in association with the chart encounter, and receiving an indication from the user that initiation of the phase is desired, the initiating component 234 is configured to initiate the designated phase of the clinical order.

The presenting component 236 was discussed herein above. By way of summary, the presenting component 236 is configured to present at least one selectable clinical order option representing an orderable clinical order. The presenting component 236 is further configured to present content associated with the orderable clinical order represented by the selectable clinical order option. In accordance with embodiments hereof, the orderable clinical order includes one or more phases associated therewith. Accordingly, the presenting component 236 is further configured to present a phase indicator for each of the phases associated with the selectable clinical order option(s). In this regard, the presenting component 236 is further configured to present content associated with a phase of the clinical order associated with a selected phase indicator, the presented content being based upon (or flexed in accordance with) the received performance location designation.

Figure 3:
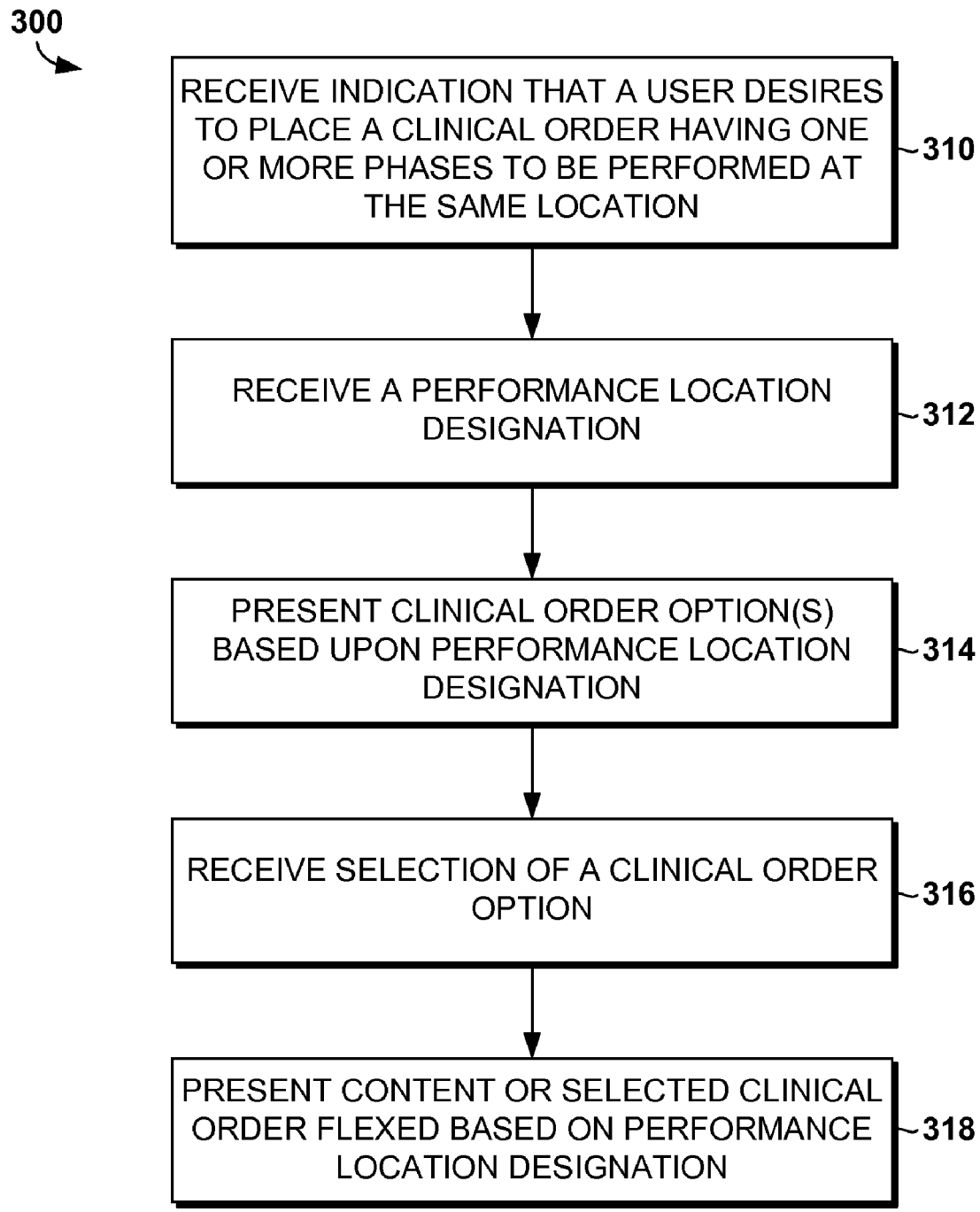
FIG. 3 is a flow diagram showing a method for permitting ordering of clinical orders to be associated with a future encounter, in accordance with an embodiment of the present invention.

Turning now to FIG. 3, a flow diagram showing a method for permitting ordering of clinical orders, in accordance with an embodiment of the present invention, is illustrated and designated generally as reference numeral 300. Method 300 may be implemented in the above-described exemplary computing system environment (FIG. 1), and, by way of example only, may be utilized by a clinician to place a clinical order having one or more phases associated therewith for a patient during a chart encounter.

Initially, as indicated at block 310, an indication is received, in association with a chart encounter associated with a first location, that a user desires to place a clinical order having one or more phases therewith, wherein each of the phases is to be performed at the same location. Such indication may be received, for instance, utilizing order-indication receiving component 218 of FIG. 2. Next, as indicated at block 312, a performance location designation to be associated with the clinical order is received (for instance, utilizing location receiving component 222 of FIG. 2). The designated performance location may be the same location as the first location or a location that differs from the location associated with the first location. Though not illustrated in FIG. 3, if desired, an indication of the encounter-type associated with the clinical order may also be received, e.g., utilizing encounter-type receiving component 220 of FIG. 2.

Based upon the performance location designation received, one or more clinical order options is presented, e.g., utilizing presenting component 236 of FIG. 2. This is indicated at block 314. Each selectable clinical order option represents an orderable clinical order having one or more phases associated therewith, each of the phases being capable of being performed at the designated performance location. Subsequently, a selection of one of the presented selectable clinical order options is received, as indicated at block 316. Such selection may be received, for instance, utilizing selection receiving component 224 of FIG. 2. Upon receiving such selection, content associated with the selected clinical order is presented, such presented content being flexed based upon the received performance location designation, for instance, utilizing presenting component 236 of FIG. 2. This is indicated at block 318.

Figure 4:
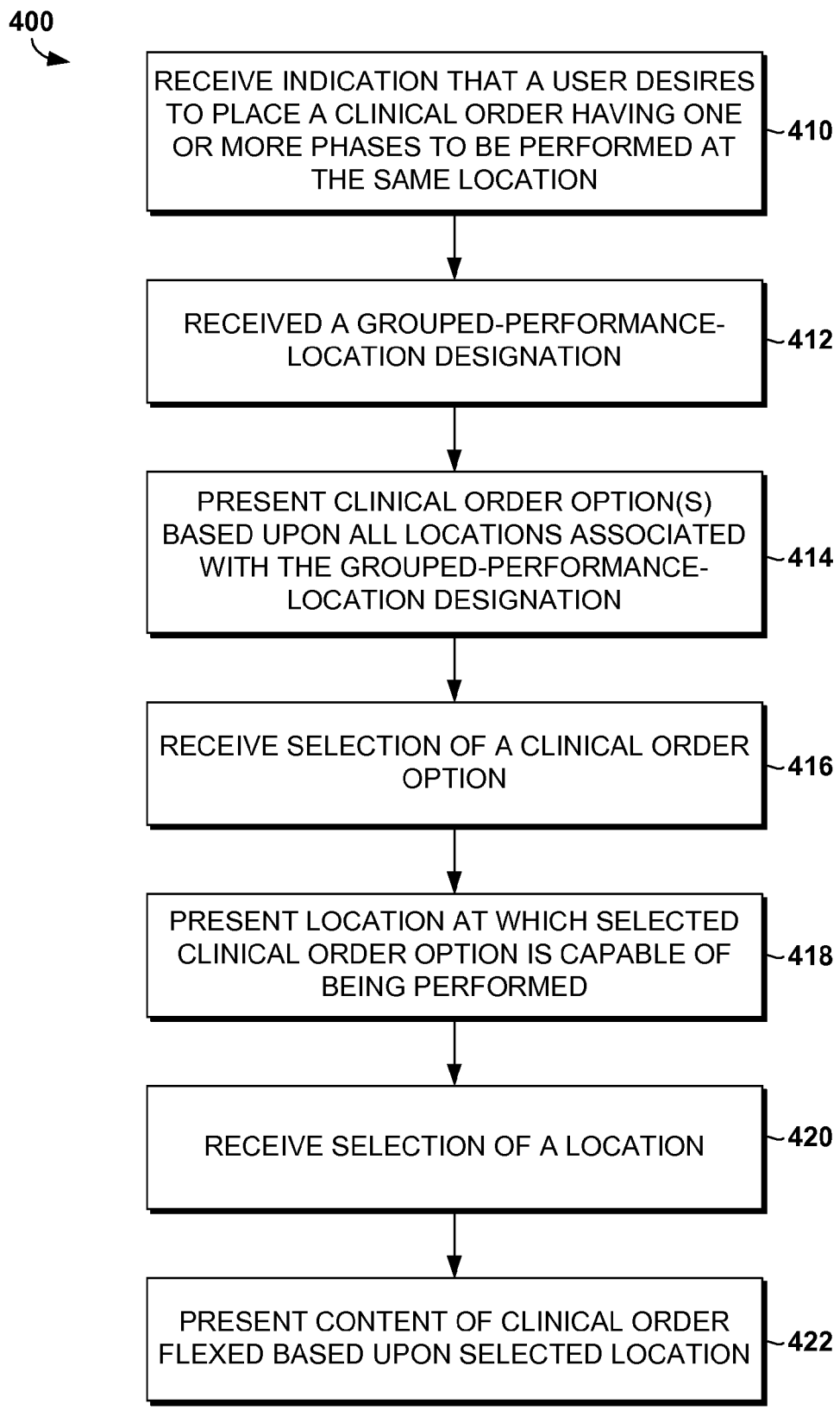
FIG. 4 is a flow diagram showing a method for permitting ordering of clinical orders to be associated with a future encounter, in accordance with an embodiment of the present invention.

Turning now to FIG. 4, a flow diagram showing a method for permitting ordering of clinical orders to be associated with a future encounter wherein a grouped performance designation is received, in accordance with an embodiment of the present invention, is illustrated and designated generally as reference numeral 400. Initially, as indicated at block 410, in association with a chart encounter associated with a first location, an indication is received that a user desires to place a clinical order, the clinical order having one or more phases associated therewith, each of the phases to be performed at the same location. Such order-indication may be received, for instance, utilizing order-indication receiving component 218 of FIG. 2. Subsequently, as indicated at block 412, a grouped-performance location designation to be associated with the clinical order is received, for instance, utilizing location receiving component 222. (Though not illustrated in FIG. 4, if desired, an encounter-type to be associated with the clinical order may also be received, for instance, utilizing encounter-type receiving component 220 of FIG. 2.) Subsequently, as indicated at block 414, at least one selectable clinical order option is presented, for instance, utilizing presenting component 236 of FIG. 2. Each presented selectable clinical order option represents an orderable clinical order each phase of which is capable of begin performed at one or more of the locations associated with the grouped-performance location designation.

Next, as indicated at block 416, selection of a one of the presented clinical order options is received, for instance, utilizing selection receiving component 224 of FIG. 2. Subsequent to receipt of a selected clinical order, each of the locations associated with the designated grouped-performance location at which the selected clinical order option is capable of being performed is presented, for instance, utilizing presenting component 236 of FIG. 2, as indicated at block 418. A selection of one of the presented performance locations is received, for instance, utilizing selection receiving component 224 of FIG. 2. This is indicated at block 420. Subsequently, as indicated at block 422, content associated with the selected clinical order is presented (e.g., utilizing presenting component 236 of FIG. 2), the content being flexed based upon the selected location.

The methods shown in the flow diagrams 300 and 400 of FIGS. 3 and 4, respectively, relate to clinical orders having phases that are all to be performed at the same location. Thus, a location designation is received only for the clinical order and then applied to each of the phases of the clinical order without further designation. As set forth previously, however, in accordance with embodiments hereof, location designations may be received on a phase-level as well if all phases of a clinical order are not to be performed at the same location. An exemplary clinical order (plan) having multiple phases, at least some of which are to be performed at locations differing from one another, is illustrated in FIG. 5. The illustrated clinical order has been described herein above.

Figure 6:
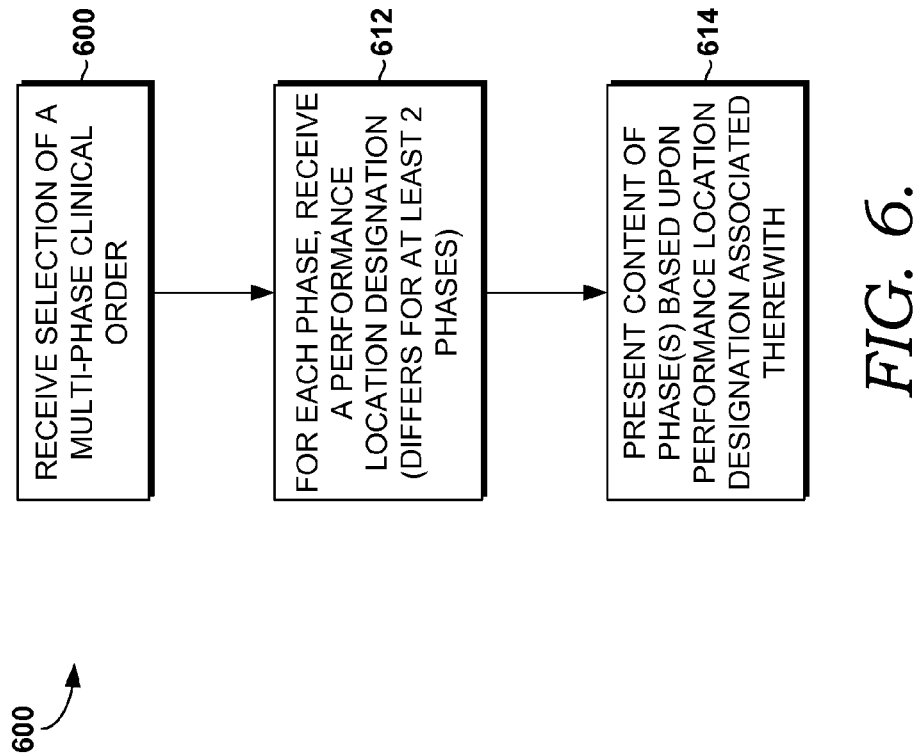
FIG. 6 is a flow diagram showing a method for presenting content associated with a multi-phase clinical order based upon a designated performance location, in accordance with an embodiment of the present invention.

Turning now to FIG. 6, a flow diagram showing a method for presenting content associated with a multi-phase clinical order based upon a designated performance location is illustrated and designated generally as reference numeral 600. Initially, as indicated at block 610, a selection of a multi-phase clinical order is received in association with a chart encounter associated with a first location, for instance, utilizing selection receiving component 224 of FIG. 2. Subsequently, as indicated at block 612, for each of the phases of the multi-phase clinical order, a performance location designation is received that represents a location at which the associated phase is to be performed, for instance, utilizing location receiving component 222 of FIG. 2. The performance locations for at least two of the phases of the multi-phase clinical order differ from one another. Next, as indicated at block 614, content associated with at least one phase of the multi-phase clinical order is presented, for instance, utilizing presenting component 236 of FIG. 2. The presented content is based upon the selected performance location associated with the presented phase(s).

Figure 7A:
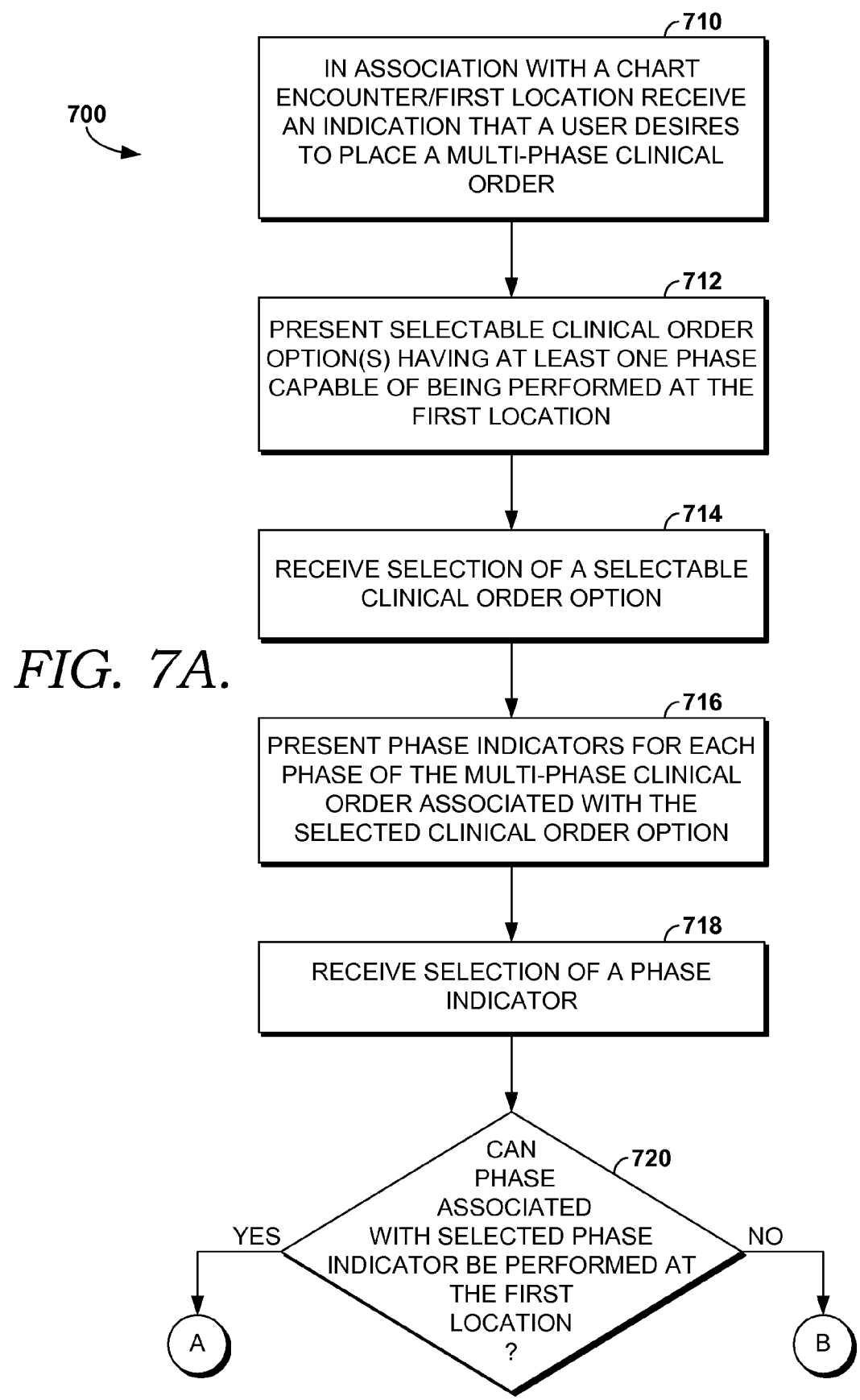
FIGS. 7A-7C are a flow diagram showing a method for presenting content associated with a multi-phase clinical order based upon a designated performance location, in accordance with an embodiment of the present invention.
Figure 7B:
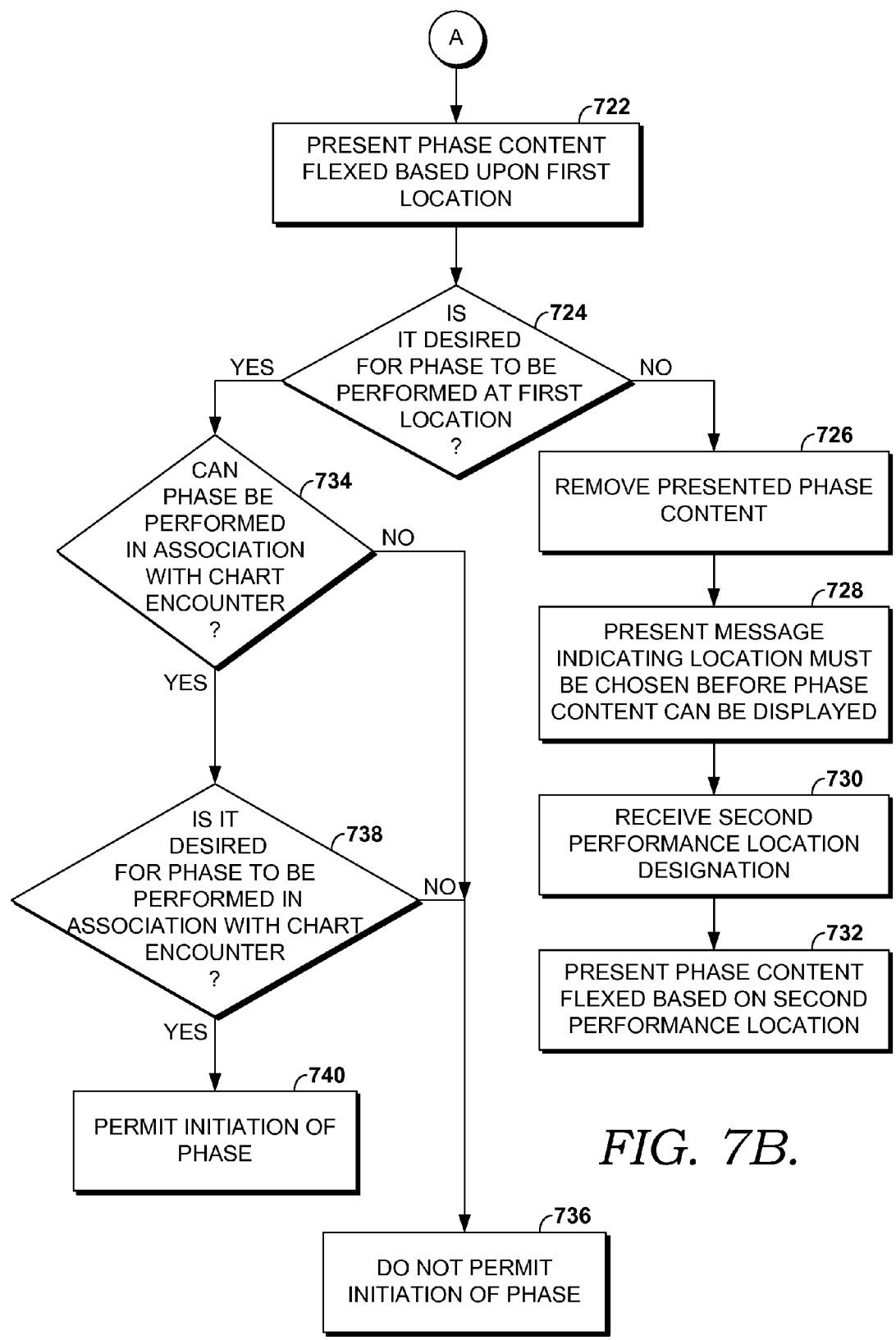
Figure 7C:
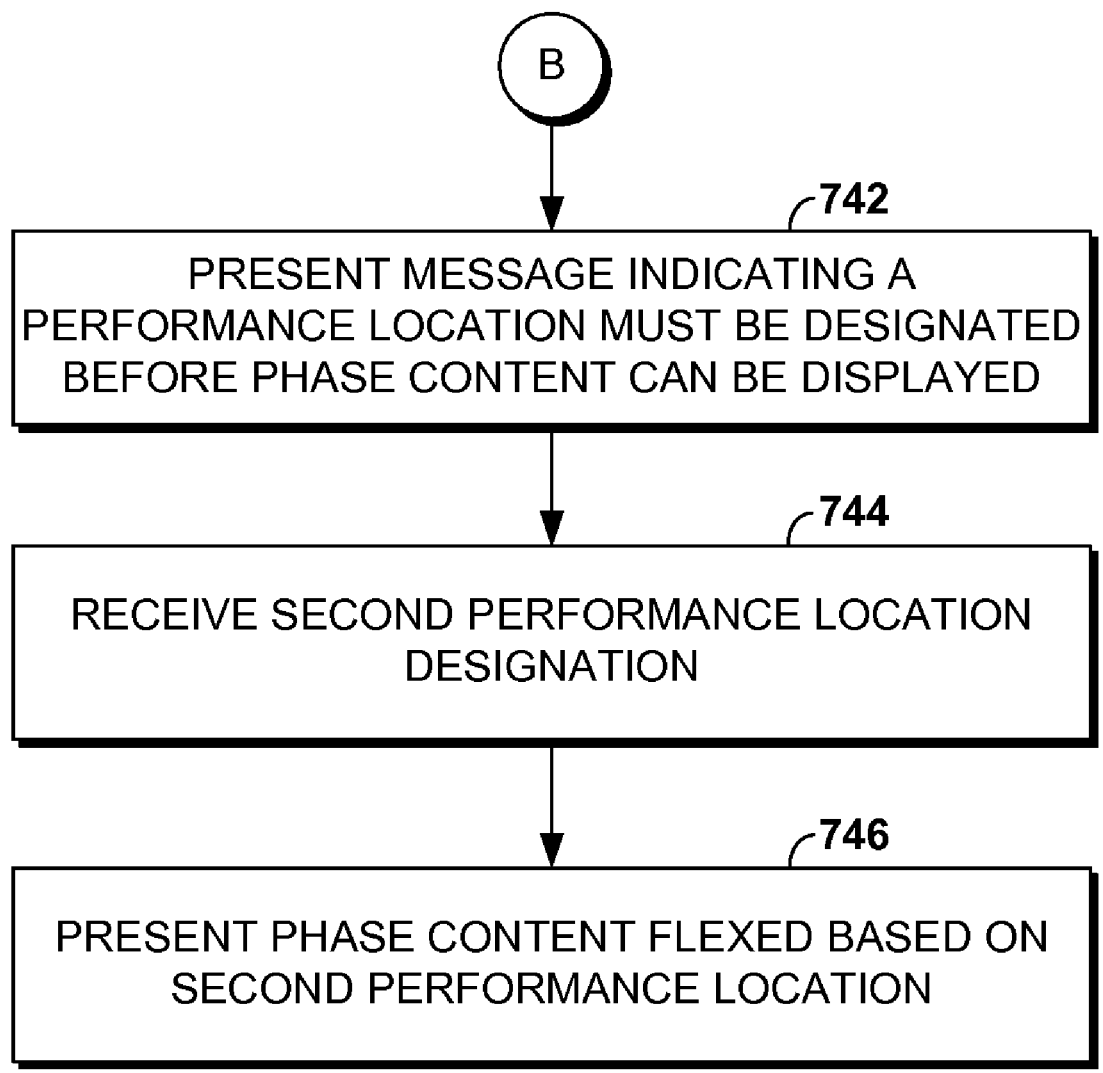

With reference to FIGS. 7A-7C, a flow diagram showing a method for presenting content associated with a multi-phase clinical order based upon a designated performance location, in accordance with an embodiment of the present invention, is illustrated and designated generally as reference numeral 700. Initially, as indicated at block 710, in association with a chart encounter associated with a first performance location, an indication that user desires to place a multi-phase clinical order is received, for instance, utilizing order-indication receiving component 218 of FIG. 2. Subsequently, as indicated at block 712, at least one selectable multi-phase clinical order option is presented, e.g., utilizing presenting component 236 of FIG. 2. Each presented selectable multi-phase clinical order option represents a multi-phase clinical order having at least one phase that is capable of being performed at the first performance location. Next, as indicated at block 714, a selection of one of the presented selectable multi-phase clinical order option is received (for instance, utilizing selection receiving component 224 of FIG. 2). Phase indicators for each phase associated with the selected multi-phase clinical order option are subsequently presented (e.g., utilizing presenting component 236), as indicated at block 716. Selection of one of the presented phase indicators is subsequently received (e.g., utilizing selection receiving component 224 of FIG. 2). This is indicated at block 718.

Subsequently, as indicated at block 720, it is determined whether the phase associated with the selected phase indicator is capable of being performed at the first location (the location associated with the chart encounter). Such action may be performed, for instance, utilizing initiation-determining component 232 of FIG. 2. If it is determined that the phase associated with the selected phase indicator is capable of being performed at the first location, phase content is presented (e.g., utilizing presenting component 236 of FIG. 2) that is flexed based upon the capabilities at the first location. This is indicated at block 722. Next, as indicated at block 724, it is determined whether the user desires for the phase to be performed at the first location. Such determination may be made, for instance, by receiving a user indication of the location to be associated with the selected phase, e.g., utilizing location receiving component 222 of FIG. 2.

If it is determined that the user desires for the phase to be performed at the first location, it is next determined whether the phase can be performed in association with the chart encounter, e.g., utilizing initiation-determining component 232 of FIG. 2. This is indicated at block 734. If the selected phase cannot be performed in association with the chart encounter (for instance, if there are intervening phases that must be completed prior to initiation of the selected phase), initiation of the phase is not permitted, as indicated at block 736. If, however, it is determined that the selected phase is capable of being performed in association with the chart encounter, it is determined whether the user desires the phase to be performed in association with the chart encounter, as indicated at block 738 (for instance, utilizing initiation-determining component 232 of FIG. 2). A user may evidence such desire, for instance, by indicating an encounter-type as FUTURE or CURRENT (e.g., utilizing encounter-type receiving component 220 of FIG. 2). If it is determined that the user does not desire for the phase to be performed in association with the chart encounter, initiation of the phase is not permitted, as indicated at block 736. However, if it is determined that performance of the selected phase in association with the chart encounter is desired, initiation of the phase is permitted, as indicated at block 740.

Returning to block 724, if it is determined that the user does not desire for the phase to be performed at the first location, the presented phase content is removed, as indicated at block 726, and a message indicating that a location must be chosen before the phase content can be displayed is presented (e.g., utilizing presenting component 236 of FIG. 2), as indicated at block 728. A user may evidence a desire for the phase to be performed at a location other than the first location, for instance, by designating a performance location that differs from that of the first location, for instance, utilizing location receiving component 222. The second performance location is subsequently received, as indicated at block 730, for instance, utilizing location receiving component 222 of FIG. 2. Note that such location may have already been received as evidence of the user's desire for the selected to be performed at a location other than the first location. In such circumstance, the step indicated at block 730 may be performed in conjunction with block 724 and block 728 is not necessary. Once a performance location has been designated, content of the selected phase is presented to the user, the content being flexed based upon the second performance location, for instance, utilizing presenting component 236 of FIG. 2. This is indicated at block 732.

Returning now to block 720 of FIG. 7A, if it is determined that the phase associated with the selected phase indicator cannot be performed at the first location, a message indicating a performance location must be designated prior to displaying content of the selected phase is presented to the user, for instance, utilizing presenting component 236 of FIG. 2. This is indicated at block 742. Subsequently, a second performance location designation, differing from the first location, is received (for instance, utilizing location receiving component 222 of FIG. 2). This is indicated at block 744. Once a performance location has been designated, content of the selected phase is presented to the user, the content being flexed based upon the second performance location, for instance, utilizing presenting component 236 of FIG. 2. This is indicated at block 746.

As can be understood, embodiments of the present invention provide computerized methods and systems for permitting clinicians and other healthcare providers to designate performance locations for clinical orders having one or more phases associated therewith, and to presenting order catalog content that is flexed based upon the designated performance location for the clinical order. Embodiments of the present invention further provide computerized methods and systems for permitting clinicians and other healthcare providers to designate a performance location for each phase of a multi-phase clinical order, and to presenting order catalog content for each phase that is flexed based upon the designated performance location for the phase. Additionally, embodiments of the present invention provide control of plan and phase initiation based at least upon a location associated with the chart encounter.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more computer-readable storage media having computer-executable instructions embodied thereon for performing a method in a clinical computing environment for permitting ordering of clinical orders to be associated with a future encounter at a designated performance facility, the method comprising:
   receiving, in association with a chart encounter associated with a first performance facility, a single clinical order inputted by a single user, the single clinical order having one or more phases associated therewith;
   determining that a first phase of the one or more phases is locationally-associated with a second phase of the one or more phases;
   receiving a single performance facility designation to be associated with the first phase of the single clinical order, the single performance facility designation being a second performance facility that differs from the first performance facility;
   based on the first phase being locationally-associated with the second phase, associating the single performance facility designation with the second phase of the single clinical order;
   enforcing the association of the single performance facility designation with the second phase such that altering the performance facility designation for the first phase or the second phase of the single clinical order also alters the performance facility designation for other phases that are locationally-associated with the respective altered first phase or second phase;
   accessing a data store, the data store comprising at least one or more relationships between facilities and clinical orders associated therewith and relationships between facilities and a phase of a clinical order associated therewith;
   using the data store, determining based on the single performance facility designation at least one selectable clinical order option, the at least one selectable clinical order option representing an orderable clinical order having one or more phases associated therewith, each of the one or more phases having a plurality of orders associated therewith; and
   presenting the at least one selectable clinical order option on a user interface.

2. The one or more computer-readable storage media of claim 1, wherein the method further comprises receiving an indication that the single clinical order is to be performed in association with a future encounter.

3. The one or more computer-readable storage media of claim 1, wherein the method further comprises:
receiving a selection of one of the at least one selectable clinical order options; and
presenting content associated with the orderable clinical order represented by the selected clinical order option.

4. The one or more computer-readable storage media of claim 3, wherein presenting content associated with the orderable clinical order represented by the selected clinical order option comprises presenting a phase indicator for each of the one or more phases associated with the orderable clinical order represented by the selected clinical order option.

5. The one or more computer-readable storage media of claim 4, further comprising receiving phase-level individualization information for the orderable clinical order represented by the selected clinical order option.

6. The one or more computer-readable storage media of claim 4, wherein the method further comprises receiving a selection of the phase indicator for one of the one or more phases, and wherein presenting content associated with the orderable clinical order represented by the selected clinical order option further comprises presenting content associated with the phase represented by the selected phase indicator.

7. The one or more computer-readable storage media of claim 6, further comprising receiving detail-level individualization information for the phase represented by the selected phase indicator.

8. The one or more computer-readable storage media of claim 1, wherein receiving a performance facility designation to be associated with the clinical order comprises receiving the performance facility designation from a list of allowable performance facilities associated with the user.

9. One or more computer-readable storage media having computer-executable instructions embodied thereon for performing a method in a clinical computing environment for permitting ordering of clinical orders to be associated with a future encounter at a designated performance facility, the method comprising:
receiving, in association with a chart encounter associated with a first performance facility, a single clinical order inputted by a single user, the single clinical order having a plurality of phases associated therewith;
determining that a first phase of the plurality of phases is locationally-associated with a second phase of the plurality of phases;
receiving a performance facility designation to be associated with the first phase, the performance facility designation received from a list of allowable performance facilities associated with the single user;
based on the first phase being locationally-associated with the second phase, associating the performance facility designation with the second phase of the single clinical order;
enforcing the association of the performance facility designation with the second phase such that altering the performance facility designation for the first phase or the second phase of the single clinical order also alters the performance facility designation for other phases that are locationally-associated with the respective altered first phase or second phase;
receiving an indication that the single clinical order is to be performed in association with a future encounter;
accessing a data store, the data store comprising at least one or more relationships between facilities and clinical orders associated therewith and relationships between facilities and a phase of a clinical order associated therewith;
using the data store, determining based on the performance facility designation at least one selectable clinical order option, each selectable clinical order option representing an orderable clinical order having a plurality of phases associated therewith; and
presenting the at least one selectable clinical order option on a user interface.

10. The one or more computer-readable storage media of claim 9, wherein the designated performance facility is a second performance facility that differs from the first performance facility.

11. The one or more computer-readable storage media of claim 9, wherein the method further comprises:
receiving a selection of one of the at least one selectable clinical order options; and
presenting content associated with the orderable clinical order represented by the selected clinical order option.

12. The one or more computer-readable storage media of claim 11, wherein presenting content associated with the orderable clinical order represented by the selected clinical order option comprises presenting a phase indicator for each of the plurality of phases associated with the orderable clinical order represented by the selected clinical order option.

13. The one or more computer-readable storage media of claim 12, further comprising receiving phase-level individualization information for the orderable clinical order represented by the selected clinical order option.

14. The one or more computer-readable storage media of claim 12, wherein the method further comprises receiving a selection of the phase indicator for one of the plurality of phases, and wherein presenting content associated with the orderable clinical order represented by the selected clinical order option further comprises presenting content associated with the phase represented by the selected phase indicator.

15. The one or more computer-readable storage media of claim 14, further comprising receiving detail-level individualization information for the phase represented by the selected phase indicator.

16. A method utilizing a processor and memory for permitting ordering of clinical orders to be associated with a future encounter at a designated performance facility, the method comprising:
receiving, in association with a chart encounter associated with a first performance facility, a single clinical order inputted by a single user, the single clinical order having one or more phases associated therewith;
determining that a first phase of the one or more phases is locationally-associated with a second phase of the one or more phases;
receiving a grouped-performance-facility designation to be associated with the first phase, the grouped-performance-facility designation comprising a plurality of facilities associated with the single user;
based on the first phase being locationally-associated with the second phase, associating the grouped-performance-facility designation with the second phase;
enforcing the association of the grouped-performance-facility designation with the second phase such that altering the grouped-performance-facility designation for the first phase of the single clinical order or the second phase of the single clinical order also alters the grouped-performance-facility designation for other phases that are locationally-associated with the respective altered first phase or second phase;
accessing a data store, the data store comprising at least one or more relationships between facilities and a phase of a clinical order associated therewith;

using the data store and the processor, determining based on the grouped-performance-facility designation at least one selectable clinical order option, each selectable clinical order option representing an orderable clinical order each phase of which is to be performed at one or more of a plurality of performance facilities associated with the grouped-performance facility designation; and presenting the at least one selectable clinical order option on a user interface.

17. The method of claim 16, further comprising:

receiving a selection of one of the at least one selectable clinical order options; and presenting each of the plurality of performance facilities at which the selected clinical order option is capable of being performed.

18. The method of claim 17, further comprising receiving a selection of one of the plurality of presented performance facilities.

19. The method of claim 16, further comprising:

receiving a selection of one of the at least one selectable clinical order options; and presenting content associated with the orderable clinical order represented by the selected clinical order option.

20. The method of claim 19, wherein presenting content associated with the orderable clinical order represented by the selected clinical order option comprises presenting a phase indicator for each of the one or more phases associated with the orderable clinical order represented by the selected clinical order option.

21. The method of claim 20, further comprising receiving phase-level individualization information for the orderable clinical order represented by the selected clinical order option.

22. The method of claim 20, further comprising receiving a selection of the phase indicator for one of the one or more phases, and wherein presenting content associated with the orderable clinical order represented by the selected clinical order option further comprises presenting content associated with the phase represented by the selected phase indicator.

23. The method of claim 22, further comprising receiving detail-level individualization information for the phase represented by the selected phase indicator.

24. A system in a clinical computing environment for permitting ordering of clinical orders to be associated with a future encounter at a designated performance facility, the system comprising:

a computing device associated with one or more processors and one or more computer-readable storage media;

a server; and a data store coupled with the server, wherein the server:

receives, in association with a chart encounter associated with a first performance facility, a single clinical order inputted by a single user, the single clinical order having one or more phases associated therewith;

determines that a first phase of the one or more phases is locationally-associated with a second phase of the one or more phases;

receives an indication that the single clinical order is to be performed in association with a future encounter;

receives a first performance facility designation associated with the single user, the first performance facility designation to be associated with the first phase of the single clinical order;

based on the first phase being locationally-associated with the second phase, associates the first performance facility designation with the second phase;

enforces the association of the first performance facility designation with the second phase such that altering a performance facility designation for the first phase or the second phase also alters the performance facility designation for other phases that are locationally-associated with the respective altered first phase or second phase;

determines based on the first performance facility designation at least one selectable clinical order option, each selectable clinical order option representing an orderable clinical order having one or more phases associated therewith; and presents the at least one selectable clinical order option.

25. The system of claim 24, wherein the server further:

receives a selection of one of the at least one selectable clinical order options, and presents content associated with the orderable clinical order represented by the selected clinical order option.

* * * * *